US009131998B2

(12) United States Patent
Carlson et al.

(10) Patent No.: US 9,131,998 B2
(45) Date of Patent: Sep. 15, 2015

(54) DISPENSING ASSEMBLIES, ARRAYS AND SYSTEMS FOR DENTAL ARTICLES

(75) Inventors: Casey L. Carlson, Edina, MN (US); Katie B. Thompson, River Falls, WI (US); Gopal B. Haregoppa, Woodbury, MN (US); Armineh Khachatoorian, La Crescenta, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 1157 days.

(21) Appl. No.: 13/128,036

(22) PCT Filed: Oct. 23, 2009

(86) PCT No.: PCT/US2009/061768
§ 371 (c)(1),
(2), (4) Date: May 6, 2011

(87) PCT Pub. No.: WO2010/056482
PCT Pub. Date: May 20, 2010

(65) Prior Publication Data
US 2011/0212412 A1    Sep. 1, 2011

Related U.S. Application Data

(60) Provisional application No. 61/114,483, filed on Nov. 14, 2008.

(51) Int. Cl.
*A61B 19/02* (2006.01)
*A61C 19/02* (2006.01)
(52) U.S. Cl.
CPC ............. *A61C 19/02* (2013.01); *A61C 2202/00* (2013.01)

(58) Field of Classification Search
CPC ....... A61C 19/02; A61C 2202/00; A61C 7/12
USPC ............... 206/369, 368, 460, 63.5, 526, 565; 221/67, 92, 191, 209, 124, 130; 222/522, 205; 433/9, 79
See application file for complete search history.

(56) References Cited

U.S. PATENT DOCUMENTS

| | | | |
|---|---|---|---|
| 5,172,809 A * | 12/1992 | Jacobs et al. | 206/368 |
| 5,183,403 A * | 2/1993 | Masuhara et al. | 433/9 |
| 5,221,202 A * | 6/1993 | James | 433/9 |
| 5,328,363 A | 7/1994 | Chester | |
| 5,350,059 A | 9/1994 | Chester | |
| 5,354,199 A | 10/1994 | Jacobs | |
| 5,538,129 A | 7/1996 | Chester | |
| 5,636,736 A | 6/1997 | Jacobs | |

(Continued)

OTHER PUBLICATIONS

International Search Report for PCT/US2009/061768, mailed Apr. 29, 2010, 5 pages.

*Primary Examiner* — Mickey Yu
*Assistant Examiner* — Chun Cheung
(74) *Attorney, Agent, or Firm* — Kevin W. Weber

(57) ABSTRACT

Dispensing assemblies for dental articles such as orthodontic brackets include a supply tube having a generally omega-shaped configuration. The supply tube receives a carrier strip as well as a number of containers that are releasably connected to the carrier strip. A dispenser array includes a plurality of supply tubes that are coupled to a spline by connectors. A dispensing system includes a mechanism for selectively positioning an array of supply tubes in either an upright orientation for storage or alternatively in an inclined orientation for dispensing.

16 Claims, 16 Drawing Sheets

(56) References Cited

U.S. PATENT DOCUMENTS

| | | |
|---|---|---|
| 5,692,896 A | 12/1997 | Pospisil |
| 6,089,861 A | 7/2000 | Kelly |
| 6,183,249 B1 | 2/2001 | Brennan |
| 6,528,555 B1 | 3/2003 | Nikutowski |
| 7,264,117 B2 | 9/2007 | Atkin |
| 2003/0196914 A1 | 10/2003 | Tzou |
| 2008/0044787 A1 | 2/2008 | Cinader, Jr. |
| 2008/0286710 A1 | 11/2008 | Cinader, Jr. |

* cited by examiner

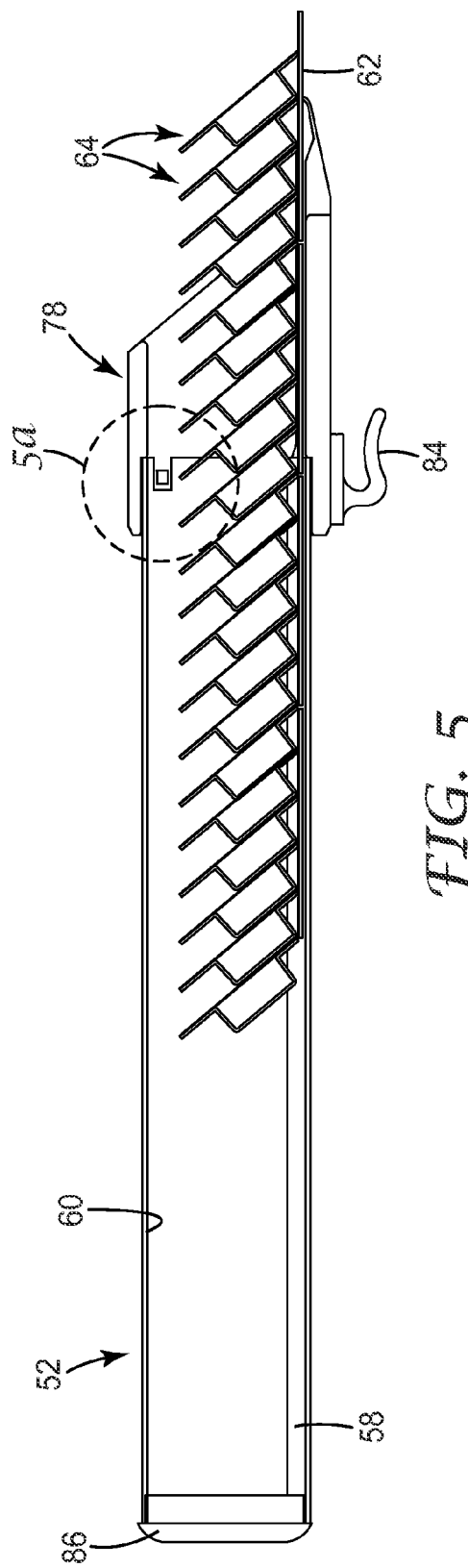
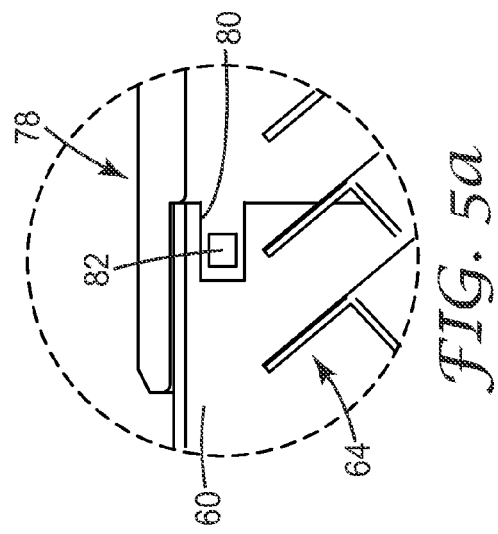
FIG. 5
FIG. 5a

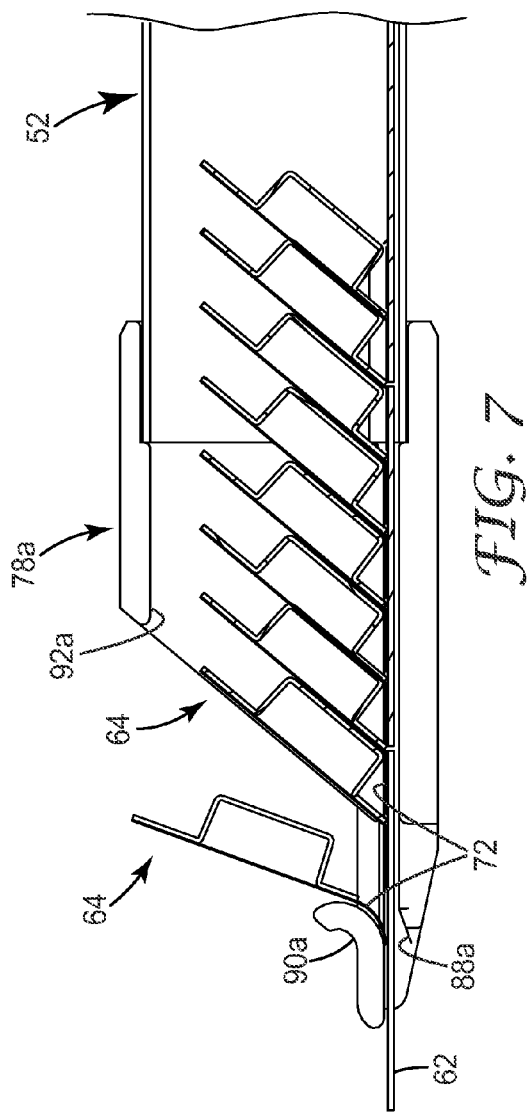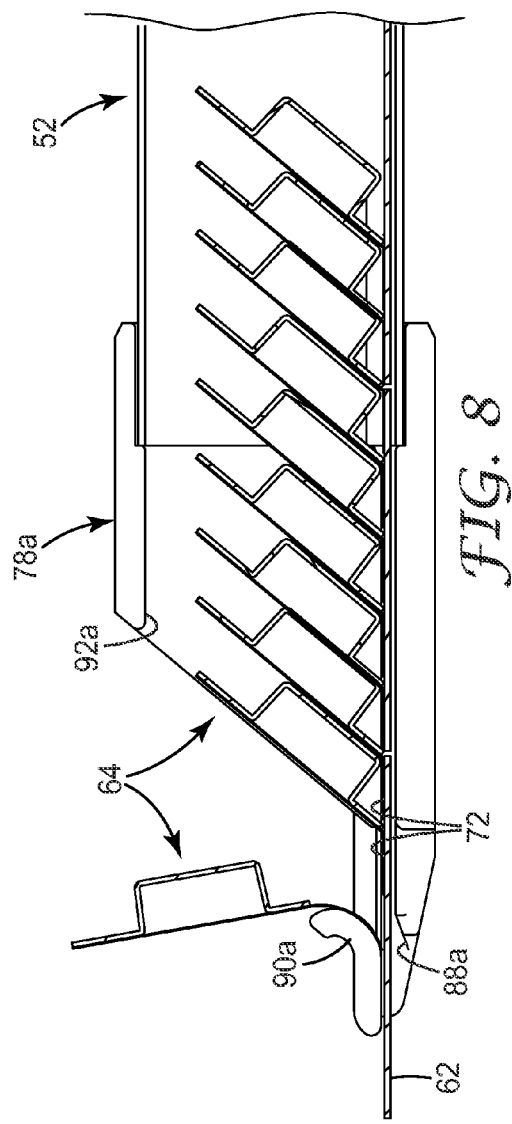

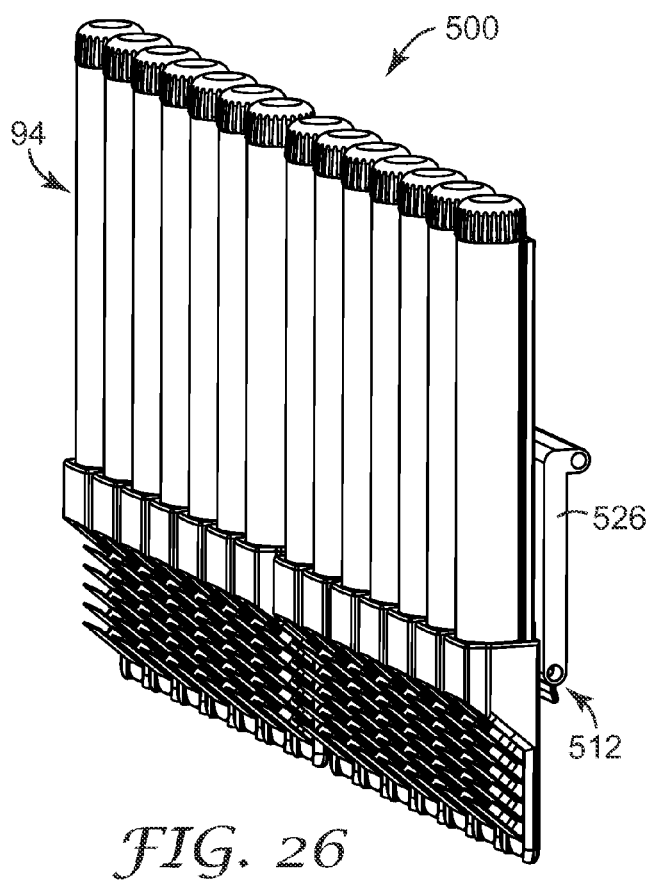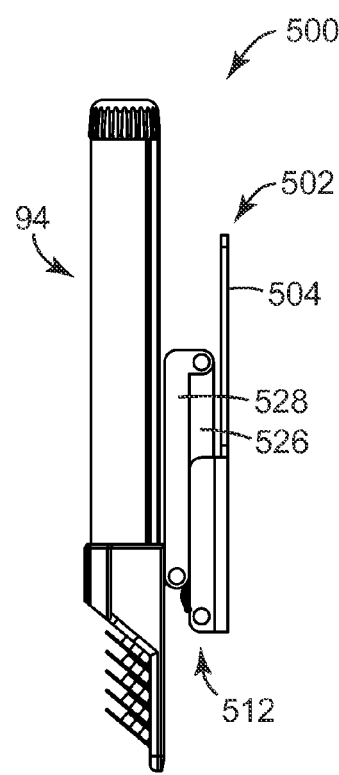
FIG. 26
FIG. 27
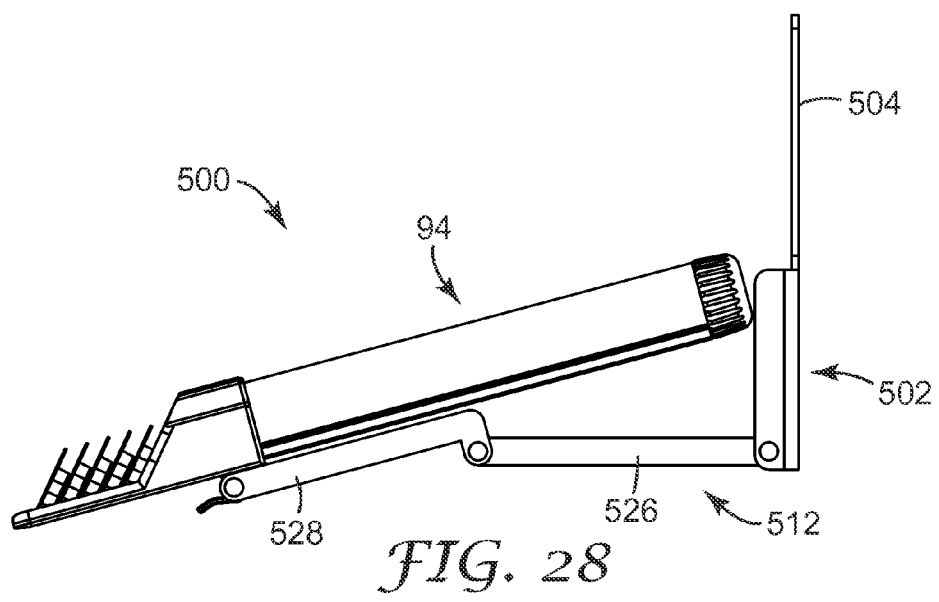
FIG. 28

DISPENSING ASSEMBLIES, ARRAYS AND SYSTEMS FOR DENTAL ARTICLES

CROSS REFERENCE TO RELATED APPLICATIONS

This application is a national stage filing under 35 U.S.C. 371 of PCT/US2009/061768, filed Oct. 23, 2009, which claims priority to U.S. Application No. 61/114,483 filed Nov. 14, 2008, the disclosures of which are incorporated by reference in their entirety herein.

BACKGROUND OF THE INVENTION

1. Field of the Invention

This invention relates to assemblies, arrays and systems that are especially useful for dispensing individually packaged dental articles such as orthodontic appliances.

2. Description of the Related Art

Dental articles that are sold to dental professionals are often individually packaged by manufacturers in sealed containers. These types of containers can be shipped and handled without undue fear of exposing dental articles within the containers to dust, debris or other contaminants. Individually packaged dental articles are particularly beneficial for large dental offices that tend to treat more than one patient at a time, since the sealed containers help ensure that cross-contamination between patients does not occur as a result of staff members handling multiple articles for different patients.

One well-known type of an individually packaged dental article is an orthodontic appliance that has been pre-coated with a light-curable adhesive for bonding the appliance to a patient's tooth. Examples of adhesive precoated appliances include orthodontic brackets and buccal tubes, both of which once fixed in place can serve as handles for controlling movement of the underlying tooth. Typically, orthodontic brackets and buccal tubes have slots or passages for receiving an orthodontic archwire, and the archwire serves as a track to guide crooked teeth toward desired, aesthetically-pleasing positions during the course of treatment.

The shapes of teeth vary widely from tooth to tooth, and also can vary from patient to patient. In addition, orthodontic malocclusions tend to be different from patient to patient. As a result, orthodontic appliances are sold in a large number of different configurations so that the practitioner is able to select a custom set of suitable appliances for best treating each patient that is encountered. Furthermore, orthodontic appliances are available in a number of different materials such as stainless steel, ceramic and composite materials. Consequently, many orthodontic practitioners maintain an inventory of a large number of different appliances so that the practitioner is able to select desired appliances without waiting for a shipment from a manufacturer or vendor.

SUMMARY OF THE INVENTION

The present invention relates to dispensing assemblies, dispenser arrays and dispensing systems that facilitate managing and dispensing an inventory of articles such as dental appliances that are individually packaged in separate containers. The invention is particularly advantageous in that the articles can be conveniently stored in compact arrangements in order to facilitate reducing the amount of space needed for storage while remaining visible for enabling a visual determination of inventory levels. The compact arrangements are also very beneficial during a dispensing operation that takes place in a dental office where countertop or other work space is limited.

In more detail, the invention in one aspect is related to a dispensing assembly for dental articles. The assembly comprises a carrier strip having a generally flat configuration and a plurality of containers each releasably connected to the carrier strip. The assembly includes a plurality of dental articles, and each dental article is received in a respective one of the containers. The assembly further includes a supply tube including a housing having a longitudinal axis and a chamber extending along the longitudinal axis. The chamber includes a base portion having a generally rectangular configuration when viewed in reference planes perpendicular to the longitudinal axis and an upper portion having a generally circular configuration when viewed in reference planes perpendicular to the longitudinal axis. The base portion is in communication with the upper portion and receives the carrier strip. The carrier strip is slidable along the base portion in directions along the longitudinal axis, and the containers extend into the upper portion.

Another aspect of the invention is directed to a dispenser array that comprises a plurality of elongated supply tubes and a quantity of containers received in each of the supply tubes. The array also includes a plurality of dental articles, and each article is received in a respective one of the containers. The array includes a plurality of dispensing heads, and each dispensing head is connected to a respective one of the supply tubes. The array further includes an elongated spline and a plurality of connectors for arranging the supply tubes in a row in side-by-side relationship to each other. Each of the connectors releasably connects the spline to a corresponding one of the dispensing heads or its respective supply tube.

The invention is also directed in another aspect to a dispensing system for dental articles. The system comprises an array of elongated supply tubes arranged along a row in side-by-side relationship to each other and a quantity of containers received in the supply tubes. The system also comprises a plurality of dental articles each received in a respective one of the containers, and a base for supporting the array of supply tubes. The base includes a mechanism for selectively supporting the array in either an upright orientation for storage and alternatively in an inclined orientation for dispensing. Further details of the invention are defined in the features of the claims.

BRIEF DESCRIPTION OF THE DRAWINGS

FIG. 5 is a reduced side cross-sectional view of the dispensing assembly and dispensing head depicted in FIG. 4;

FIG. 5a is an enlarged side cross-sectional view of a portion of the dispensing assembly with the dispensing head shown in FIG. 5;

FIG. 7 is a side cross-sectional view of the dispensing assembly shown in FIG. 6;

FIG. 8 is a view somewhat similar to FIG. 7 except that FIG. 8 shows one of the containers of the dispensing assembly being released from a carrier strip of the assembly as might occur in a dispensing operation;

FIG. 26 is a perspective view of a dispensing system according to a further embodiment of the invention; illustrating the dispensing system as it might appear when not in use;

FIG. 27 is a side elevational view of the dispensing system depicted in FIG. 26;

FIG. 28 is a view somewhat similar to FIG. 27 except that the dispensing system is shown in an orientation as it might appear during a dispensing operation;

DETAILED DESCRIPTION OF THE PREFERRED EMBODIMENTS

Figure 1:
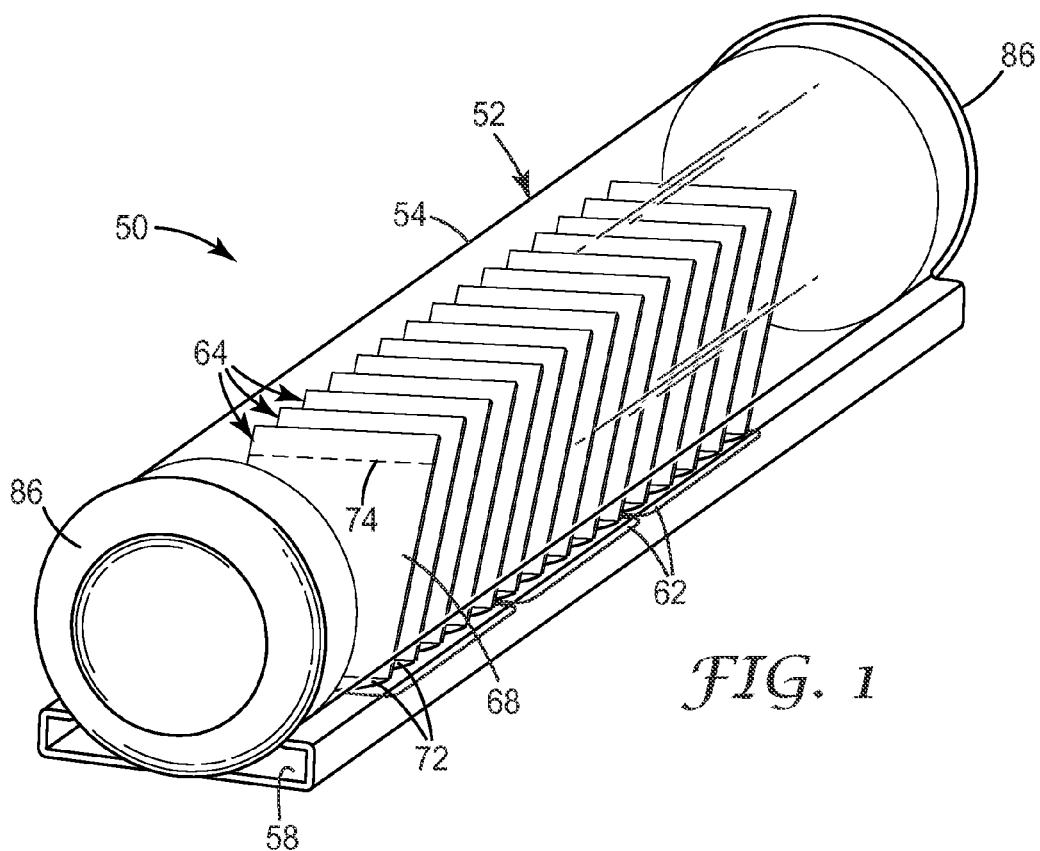
FIG. 1 is perspective view of a dispensing assembly constructed in accordance with one embodiment of the present invention.
Figure 2:
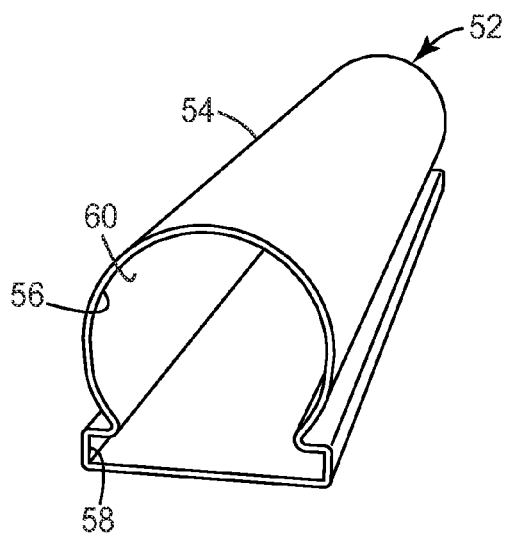
FIG. 2 is a perspective view of a supply tube of the assembly shown in FIG. 1, looking in a somewhat different direction than the view of FIG. 1.

A dispensing assembly 50 according to one embodiment of the present invention is illustrated in FIG. 1 and comprises an elongated supply tube 52 that includes a housing 54. The housing 54 is shown alone in FIG. 2 and includes an elongated chamber 56 that has a generally omega-shaped configuration when viewed in reference planes perpendicular to its longitudinal axis. The chamber 56 includes a base portion 58 having a generally rectangular configuration when viewed in reference planes perpendicular to the longitudinal axis of the chamber 56 and an upper portion 60 having a generally circular configuration when viewed in the same reference planes.

The dispensing assembly 50 also includes at least one carrier strip 62 (see, e.g., FIGS. 1 and 3) having a generally flat configuration. A plurality of containers 64 are releasably connected to the carrier strip 62. For example, five containers 64 may be connected to each carrier strip 62, and the chamber may have sufficient length to contain four carrier strips 62 each connected to five containers 64. Alternatively, the carrier strip 62 may have a relatively long length and carry, for example, ten or twenty containers 64. As another option, a secondary strip, having a length longer than the carrier strip 62, may be provided to couple a number of carrier strips together in a long row. The secondary strip may comprise a paper or plastic card extending below the carrier strips 62 with an adhesive for coupling to the carrier strips 62. Alternatively, the secondary strip may comprise a pre-formed plastic substrate with indentations, recesses or other structure that snap-fits onto edges of the carrier strips 62.

Figure 3:
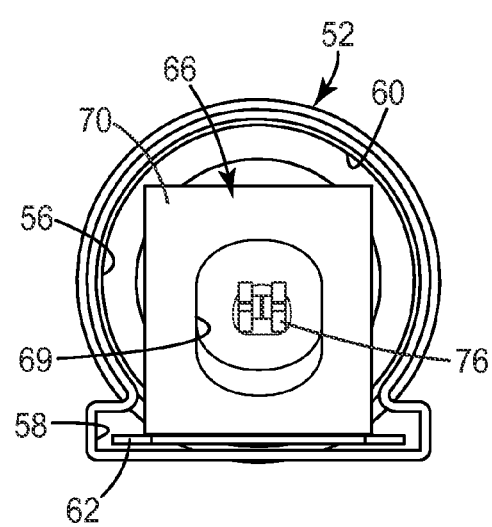
FIG. 3 is an enlarged cross-sectional view of the dispensing assembly of FIG. 1, looking in a direction along the longitudinal axis of the supply tube.

Each of the containers 64 includes a cover 68 as shown for example in FIG. 1 and a bottom portion 66 as illustrated in FIG. 3 (in FIG. 3, the cover of the container 64 has been removed for purposes of illustration). The bottom portion 66 includes an oval-shaped recess or well 69 as well as a flange 70 that surrounds the opening of the well 69. The cover 68 of each container 64 is releasably connected to a corresponding bottom portion 66 by an adhesive, a heat seal or other means. Each cover 68 includes a tab 72 that extends beyond the flange 70 in an inclined direction relative to the flange 70. The tab 72 has rounded front corners and provides a convenient handle for grasping the cover 68 when it is desired to open the container 64.

As shown in FIG. 1, the cover 68 preferably includes a line of perforations 74 that defines a front, openable cover section and a rear hinge section. When the tab 72 is grasped and pulled away from the bottom portion 66, the cover 68 is moved to an upstanding position (assuming that the bottom portion 66 extends in a horizontal plane), bent at the line of perforations 74. The perforations 74 facilitate self-retention of the cover 68 in its open, upright position and permit the cover 68 to be made of relatively stiff materials. The perforations 74 also provide tactile feedback to the user that the cover 68 is open so that the user does not continue to pull on the cover 68 and separate the rear hinge section from the flange 70 of the bottom portion 66.

Preferably, an adhesive such as a hot melt adhesive releasably connects the tab 72 of each container 64 to the carrier strip 62. Optionally, the adhesive extends in a continuous bead centrally disposed along the longitudinal axis of the upper side of the carrier strip 62, although an interrupted bead, a series of dots or another pattern of adhesive is also possible. The containers 64 when connected to the carrier strip 62 are positioned in an aligned, stacked arrangement with the containers 64 abutting each other.

Each container 64 in the stacked arrangement extends in an upward, inclined direction when the carrier strip 62 is oriented in a horizontal plane. The carrier strip 62 is received in the base portion 58 of the chamber 56, and the containers 64 extend into the upper portion 60. The base portion 58 serves as a track to guide sliding movement of the carrier strip 62 with the attached containers 64 along the longitudinal, central axis of the chamber 56.

As illustrated in FIG. 3, a dental article such as a dental appliance 76 is received in the well 69 of each container 64. In this instance, the dental appliance 76 is an orthodontic bracket. However, other dental articles and appliances are also possible, such as buccal tubes and bands as used in orthodontic treatment and dental crowns as used in the practice of general dentistry.

Preferably, the base of the orthodontic bracket appliance 76 shown in FIG. 3 is precoated with an adhesive for bonding the appliance 76 directly to the surface of a patient's tooth. Preferably, the adhesive used for precoating the appliance 76 is a light-curable, non-toxic orthodontic adhesive such as the adhesives that are described in U.S. Pat. No. 5,354,199 (Jacobs et al.) and U.S. Pat. No. 6,528,555 (Nikutowski et al.). Although not shown in the drawings, the container 64 preferably includes a release film or substrate extending along the bottom of the well 69 for facilitating separation of the adhesive from the container 64 when the appliance 76 is removed from the well 68. Examples of suitable release films and substrates are described, for example, in U.S. Pat. No. 5,328,363 (Chester et al.) and U.S. Pat. No. 6,183,249 (Brennan et al.).

Additional details of possible constructions and alternatives for the carrier strip 62 and the containers 64 are described in U.S. Pat. No. 5,328,363 (Chester et al.), U.S. Pat. No. 5,350,059 (Chester et al.), U.S. Pat. No. 5,538,129 (Chester et al.), U.S. Pat. No. 5,636,736 (Jacobs et al.), U.S. Pat. No. 6,089,861 (Kelly et al.) and published U.S. Patent Application No. 2003/0196914 (Tzou et al.). Other containers are also possible, such as those described in published U.S. Patent Application Nos. 2008/0044787 (Cinader, Jr. et al.) and US2008/0286710 (Cinader, Jr. et al.).

As an option, the supply tube 52 is made of a transparent polymeric material so that the number of containers 64 within the supply tube 52 can be visually determined. As an additional option, the supply tube is transparent and also color-coded to indicate one or more characteristics of the appliances 76 in the containers 64. For example, color-coding may be utilized to indicate the tooth (such as cuspid or bicuspid) for which the appliances 76 are intended. As another example, color-coding may be utilized to indicate the material of the appliances 76, such as whether the appliances 76 are made of ceramic, metal or composite materials.

Figure 4:
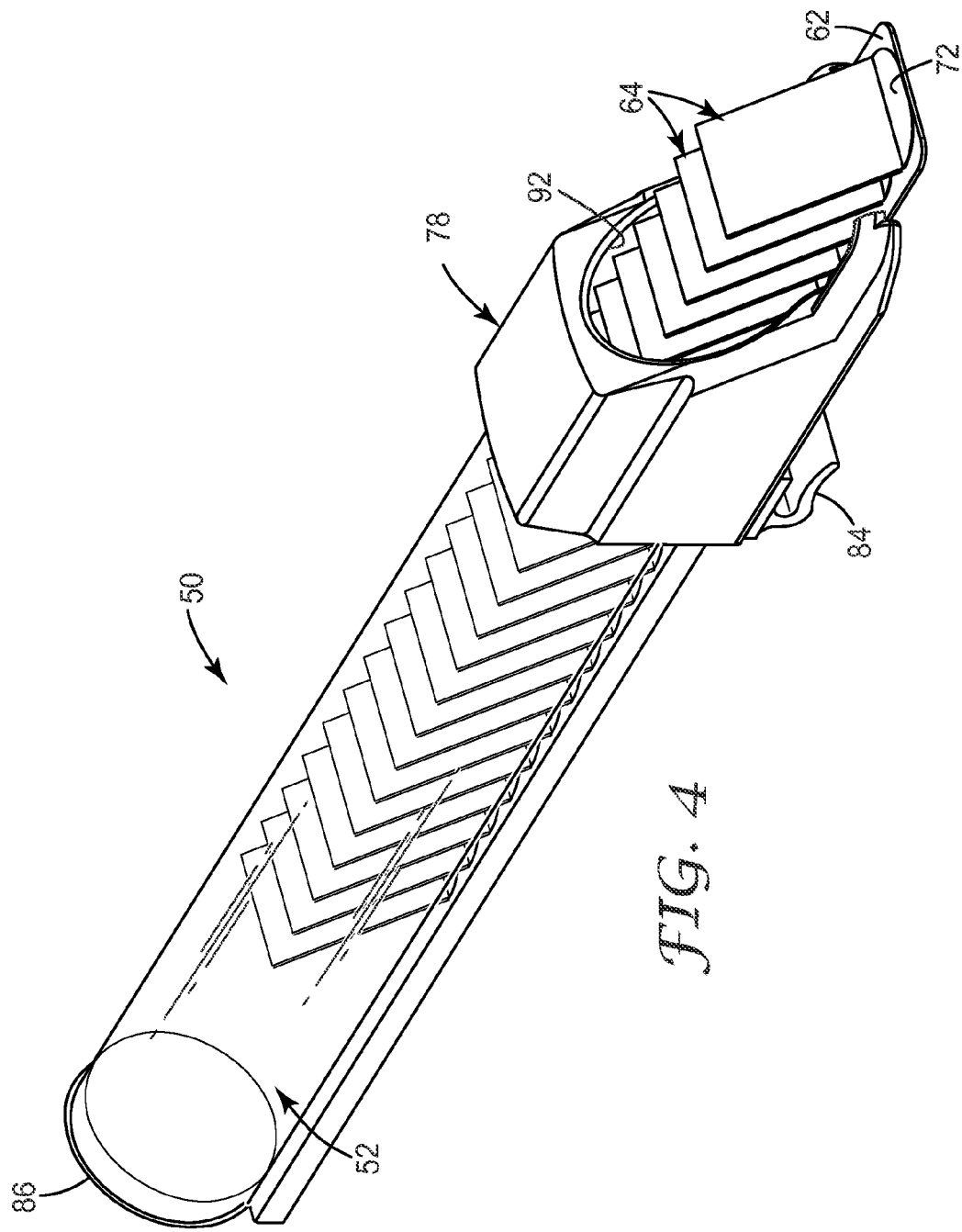
FIG. 4 is a perspective view of the dispensing assembly illustrated in FIG. 3 along with a dispensing head that is connected to the supply tube.

The dispensing assembly 50 preferably includes a dispensing head 78 such as is illustrated in the embodiment shown in FIGS. 4 and 5. The dispensing head 78 is coupled, and preferably is detachably coupled, to a forward end of the supply tube 52. A rear section of the dispensing head 78 includes a cavity for receiving the forward end of the supply tube 52 in surrounding relation. Preferably, the cavity has a generally omega-shaped configuration with a rectangular-shaped base portion and a circular-shaped upper portion, and the shape of the cavity is complemental to the omega-shaped configuration of the supply tube 52 so that the forward end of the latter is received in the cavity in mating relation with a somewhat snug fit.

Optionally, the coupling between the supply tube 52 and the dispensing head 78, which in this embodiment is established by the mating reception of the forward end of the supply tube 52 into the cavity of the dispensing head 78, also includes a keying arrangement for helping to ensure that the proper supply tube 52 is connected to the proper dispensing head 78. As shown in more detail in the enlarged view of FIG. 5a, the keying arrangement includes a keyway 80 which comprises one or more slots formed into the forward end of the supply tube 52. The keying arrangement also includes a key 82 that comprises one or more cogs that project from the dispensing head 78 into the cavity in a radial direction.

The key 82 and the keyway 80 are oriented relative to each other such that the key 82 is received in the keyway 80 when the forward end of the supply tube 52 is received in the cavity of the dispensing head 78. However, the locations of the key 82 and keyway 80 are preferably changed for different pairs of supply tubes 52 and dispensing heads 78. As a result, only a supply tube 52 having a certain keyway 80 can be coupled to a certain dispensing head 78. If, for example, an attempt was made to insert a supply tube 52 having a certain keyway 80 into the cavity of a dispensing head 78 having a non-matching key 82, the key 82 would contact the front end of the supply tube 52 and prevent the front end from entering the cavity of the dispensing head 78. Moreover, the matching omega-shaped configurations of the cavity and the forward end of the supply tube 52 would essentially render useless any attempt to couple the supply tube 52 to the dispensing head 78 by pivoting the supply tube 52 about its longitudinal axis until the key 82 and keyway 80 are aligned with each other.

Preferably, the key 82 includes a plurality of protruding cogs and the keyway 80 includes a plurality of slots, each arranged in various but matching locations along the periphery of the omega-shaped forward end of the supply tube 52 and the mating, omega-shaped cavity of the dispensing head 78. Such construction ensures that a variety of possible "combinations" for the keying arrangement are provided. This construction may also help to properly align in co-linear fashion the longitudinal axis of the supply tube 52 to the central axis of the cavity of the dispensing head 78, so that entry of the forward end of the supply tube 52 into the cavity is facilitated. As an alternative construction or as an additional construction for providing possible combinations of keying arrangements, the protrusions may have varying shapes (such as widths) and the slots may have varying shapes that match the shape of corresponding protrusions.

Preferably, the dispensing head 78 or alternatively the supply tube 52 includes a connector, the function of which will be described in the paragraphs below. In the embodiment shown in FIGS. 1-5, the connector comprises a resilient clip 84 that is fixed to the bottom of the dispensing head 78. The clip 84 has a generally "U"-shaped configuration. Other types of connectors are also possible.

The dispensing assembly 50 optionally includes one or two caps 86 that are detachably connected to the ends of the supply tube 52. If, for example, the supply tube 52 is handled separately from the dispensing head 78, it might be advantageous to cover both ends of the supply tube 52 with caps 86 as shown in FIG. 1. However, in instances where the forward end of the supply tube 52 is coupled to a dispensing head such as the dispensing head 78 shown in FIG. 4, the assembly 50 may include only one cap 86 that is connected to the rearward end of the supply tube 52.

In the embodiments shown in FIGS. 1-5, the caps 86 are connected to the supply tube 52 by a friction fit. However, other connections such as threaded connections or twist-lock connections are also possible. The caps 86 shown in the drawings have a generally cylindrical shape and cover only the upper portion 60 of the chamber 56, although as an alternative the caps 86 may instead have an omega-shaped configuration that would cover both the upper portion 60 as well as the base portion 58 of the chamber 56. An alternative construction for the caps 86 is shown in FIGS. 9-14 and 26-31, which is essentially the same construction as the construction for the caps 86 except that an extended, ridged region is provided for enhancing the user's grip.

The dispensing head 78 has a front opening 92, and the containers 64 along with the corresponding carrier strip 62 extend through the opening 92. When it is desired to dispense a container 64, the forward-most container 64 is grasped and pulled in an upward direction until the tab 72 of the container 64 detaches from the carrier strip 62. Additional containers 64 are dispensed in the same manner.

The dispensing head 78 includes opposed, inner rails that are aligned with the base portion 58 of the chamber 56 and function to guide movement of the carrier strip(s) 62 through the opening 92. The rails include a narrowed forward portion that hinders free movement of the carrier strip 62 through the opening 92. However, once all of the containers 64 have been detached from the carrier strip 62, the carrier strip 62 can be grasped by the user and pulled through the narrowed forward portion in order to remove the now-empty carrier strip from the dispensing head 78.

Figure 6:
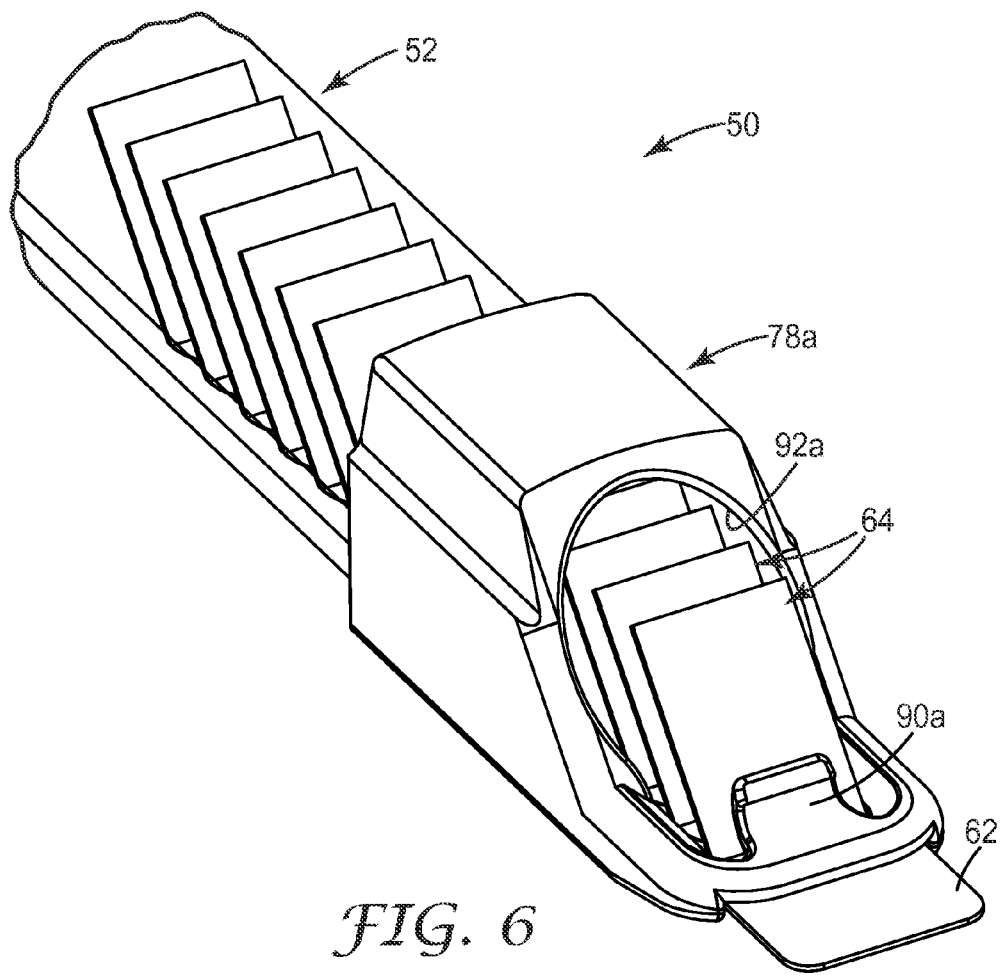
FIG. 6 is a fragmentary view illustrating an alternative dispensing head of a dispensing assembly according to another embodiment of the invention.

A dispensing head 78a according to another embodiment of the invention is illustrated in FIGS. 6-8 and includes a forward stop 90a that extends across a lower portion of a forward opening 92a. The stop 90a includes a curved section as can be appreciated by reference to FIGS. 7 and 8. The dispensing head 78a also includes opposed, inner rails 88a for guiding movement of the carrier strip 62, but in this instance the rails 88a do not include a narrowed forward portion that hinders free movement of the carrier strip through the opening. However, the forward-most container 64 contacts the rear face of the stop 90a and as a result the attached carrier strip 62 remains in contact with the dispensing head 78a until such time as all of the containers 64 have been detached from the respective carrier strip 62.

FIG. 7 illustrates an exemplary step of a dispensing operation, where the forward-most container 64 has been moved upwardly while in contact with the stop 90a. During this step, the tab of the container 64 remains connected to the carrier strip 62 and the carrier strip 62 tends to move in a rearward direction. FIG. 8 illustrates a subsequent step of the dispensing operation, where the forward-most container 64 has been moved farther away from the carrier strip 62. In FIG. 8, the tab of the container 64 has been detached from the carrier strip 62. The carrier strip 62 then advances in a forward direction until the next container 64 comes into contact with the stop 90a.

Preferably, the supply tube 52 is inclined in an orientation such that the dispensing head 78a is lower than the rear end of the supply tube 52. As a consequence, the carrier strip 62 can move freely in a forward direction along the base portion 60 of the supply tube 52 and the rails 88a of the dispensing head 78a until such time as the forward-most container 64 attached to the carrier strip 62 contacts the stop 90a. However, once all of the containers 64 have been detached from the carrier strip 62, the carrier strip 62 advances along the rails 88a until such time as it is released from the dispensing head 78a. Other aspects of the dispensing head 78a are similar to the aspects described above in connection with the dispensing head 78 and shall not be repeated.

Alternative constructions of the stop 90a are also possible. For example, the stop 90a may comprise two separate sections disposed alongside the rails 88a and spaced apart from each other. The sections contact the rounded front corners of the tab 72 as the tab 72 is detached from the carrier strip 62 during a dispensing operation, but enable a majority of the tab 72 to pass unimpeded through the space between the sections.

Figure 9:
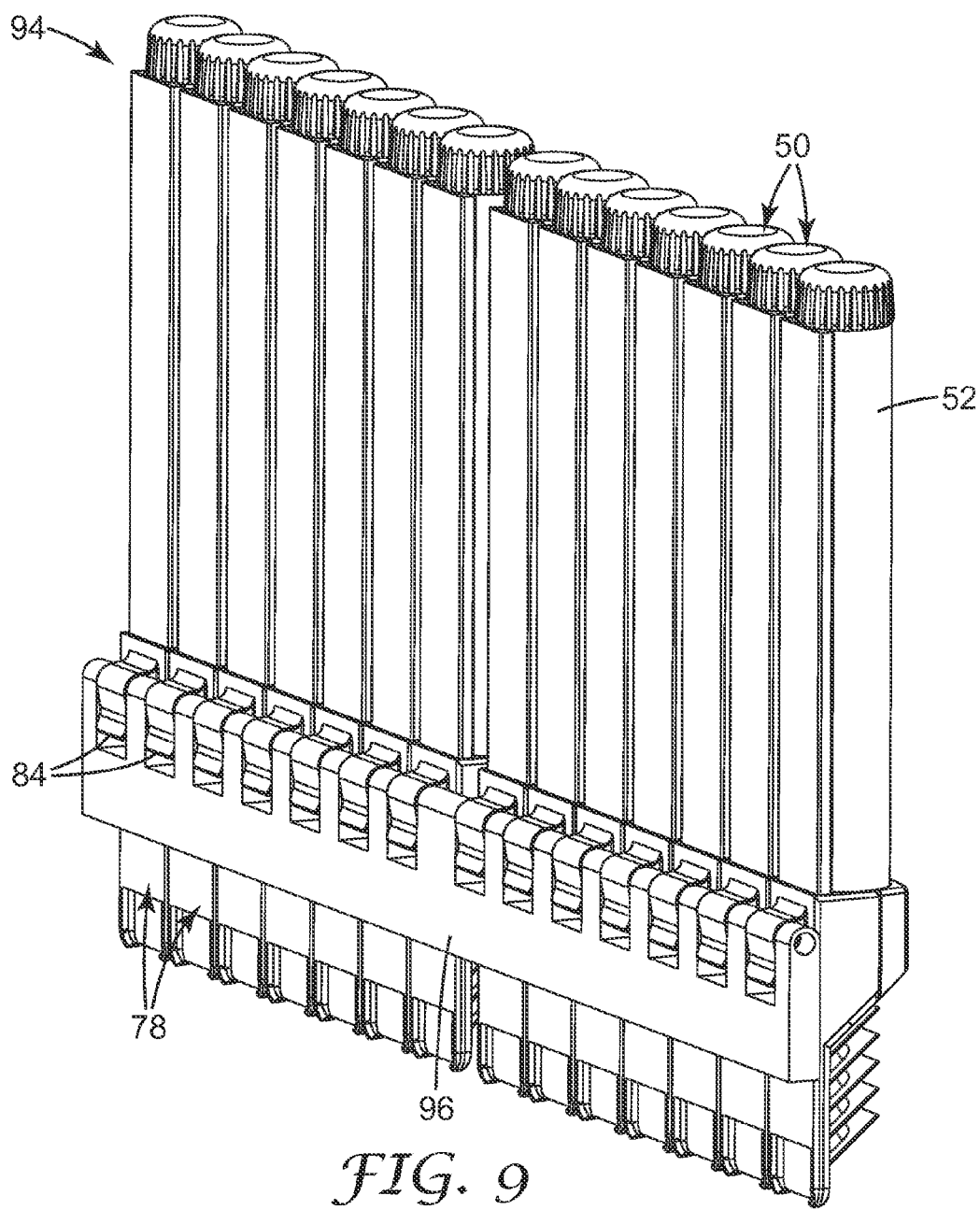
FIG. 9 is a perspective view of a dispenser array according to another aspect of the invention.

FIG. 9 is an illustration of a dispenser array 94 in accordance with another aspect of the invention. The dispenser array 94 includes an elongated spline 96, and a number of dispensing assemblies 50 are connected to the spline 96. As one option, and as shown in the drawings, the clips 84 are releasably connected to the spline 96 in snap-fit relation. Optionally, the top and/or upper side surface of the spline 96 includes a spaced-apart series of notches or recesses to provide a receptacle for receiving the clips 84 and for positioning each dispensing assembly 50 a certain, pre-selected distance away from adjacent dispensing assemblies 50. (In FIG. 9 and in the remaining figures, the caps for the supply tubes 52 have a somewhat different configuration than the caps shown in FIGS. 1, 4 and 5.)

The clips 84 in combination with the spline 96 help to arrange the supply tubes 52 in a row in side-by-side relationship to each other such that the longitudinal axes of the tubes are parallel to each other. As a result, the dispenser array 94 functions as a convenient sub-assembly that supports and arranges multiple dispensing assemblies 50 in an orderly manner. As one example, the dispensing assemblies 50 can be arranged along the spline 96 in positions that generally or exactly correspond to the ultimate positions of the appliances 76 in a set-up tray (not shown) that is assembled by the orthodontic practitioner for a patient, so that the likelihood of placing an appliance 76 in an incorrect position on the set-up tray is reduced. Examples of suitable orthodontic set-up trays and descriptions of use are set out in U.S. Pat. No. 5,692,896 (Pospisil et al.) and U.S. Pat. No. 7,264,117 (Atkin et al.).

The dispenser array 94 may have other constructions as well. For example, clips similar to clips 84 could be connected to the supply tubes 52 instead of the dispensing heads 78. As another example, the clips 84 could be replaced with other types of connectors. Moreover, the dispenser array 94 may have a smaller or greater number of dispensing assemblies 50 than the number shown in FIG. 9. Some practitioners, for example, may prefer to include dispensing assemblies 50 for bondable molar appliances, while other practitioners may prefer to use molar appliances that are fixed to bands and not dispensed using the array 94. To this end, the spline 96 may have sufficient length to support fourteen assemblies 50 as illustrated in FIG. 9, or another length to support other quantities of assembles 50 as desired. As an alternative, however, the spline 96 may have sufficient length to support on ten assemblies 50, but include end couplings that snap-fit onto additional assemblies for dispensing bondable molar appliances as may be desired by some practitioners.

A dispensing system 100 for dental articles such as the appliances 76 described above is shown in FIGS. 10-11 in accordance with another aspect of the invention. The dispensing system 100 includes a base 102 having a stand 104 for resting the system 100 on, for example, a countertop of an orthodontic laboratory or operatory. The base 102 further includes a carriage 106 that supports one or more dispensing arrays 94. In the exemplary embodiment depicted in FIGS.

10-11, two dispensing arrays 94 are connected to the carriage 106, but a smaller or greater number of arrays 94 may also be provided. For example, four arrays 94 may be provided, corresponding to the four quadrants of the dental arches. Preferably, the splines 96 of the dispensing arrays 94 are releasably connected to the carriage 106 so that multiple dispensing assemblies 50 can be connected to and disconnected from the carriage 106 as desired.

Figure 10:
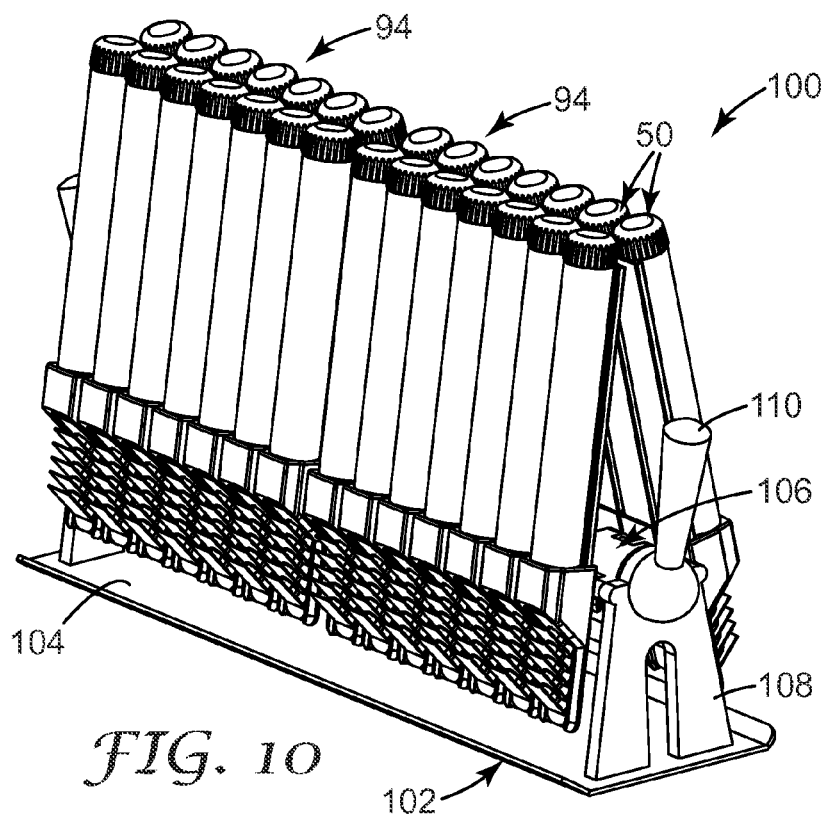
FIG. 10 is a perspective view of a dispensing system constructed according to yet another aspect of the invention, showing the system in an orientation as it might appear when in storage.
Figure 11:
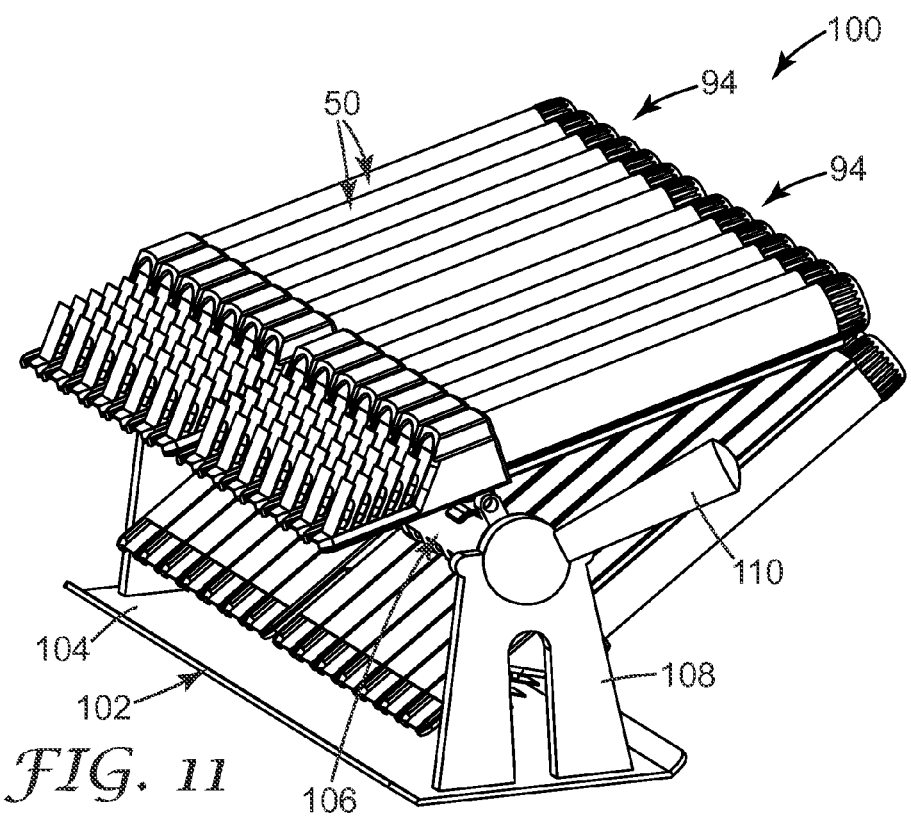
FIG. 11 is a perspective view of the dispensing system shown in FIG. 10 except that the system is shown in an orientation for dispensing.

The carriage 106 is connected to upstanding legs 108 of the stand 104 by a mechanism that in this embodiment comprises a pivot (not shown). The pivot enables pivotal movement of the carriage 106 relative to the stand 104 in an arc about a horizontal axis. A handle 110 is provided for selectively moving the carriage 106 along with the dispensing assemblies 50 between an upright orientation that is useful for storage as shown in FIG. 10 and an inclined orientation that is useful during a dispensing operation as shown in FIG. 11.

As one option, the practitioner may prefer to use the dispenser arrays 94 located on one side of the carriage 106 exclusively for orthodontic appliances 76 intended for the lower dental arch, and use the arrays 94 located on the opposite side of the carriage 106 exclusively for orthodontic appliances 76 intended for the upper dental arch. As a result, after the appliances 76 for the lower dental arch have been dispensed and placed on the set-up tray, the base 102 can be turned while resting on the countertop about a vertical axis and the handle 110 pivoted to rotate the carriage 106 about a horizontal axis. This movement will bring the other arrays 94 into a convenient orientation for dispensing appliances 76 for the upper dental arch.

Optionally, the carriage 106 may also be pivoted to an orientation such that the dispensing assemblies 50 extend along a horizontal plane. In this orientation, the supply tubes 52 can be readily refilled by removing the cap 86 from the rear end of the supply tubes 52. As an alternative, the supply tubes 52 may be disconnected from their respective dispensing heads 78 and replaced with new supply tubes 52 that have been previously filled with containers 64.

Figure 12:
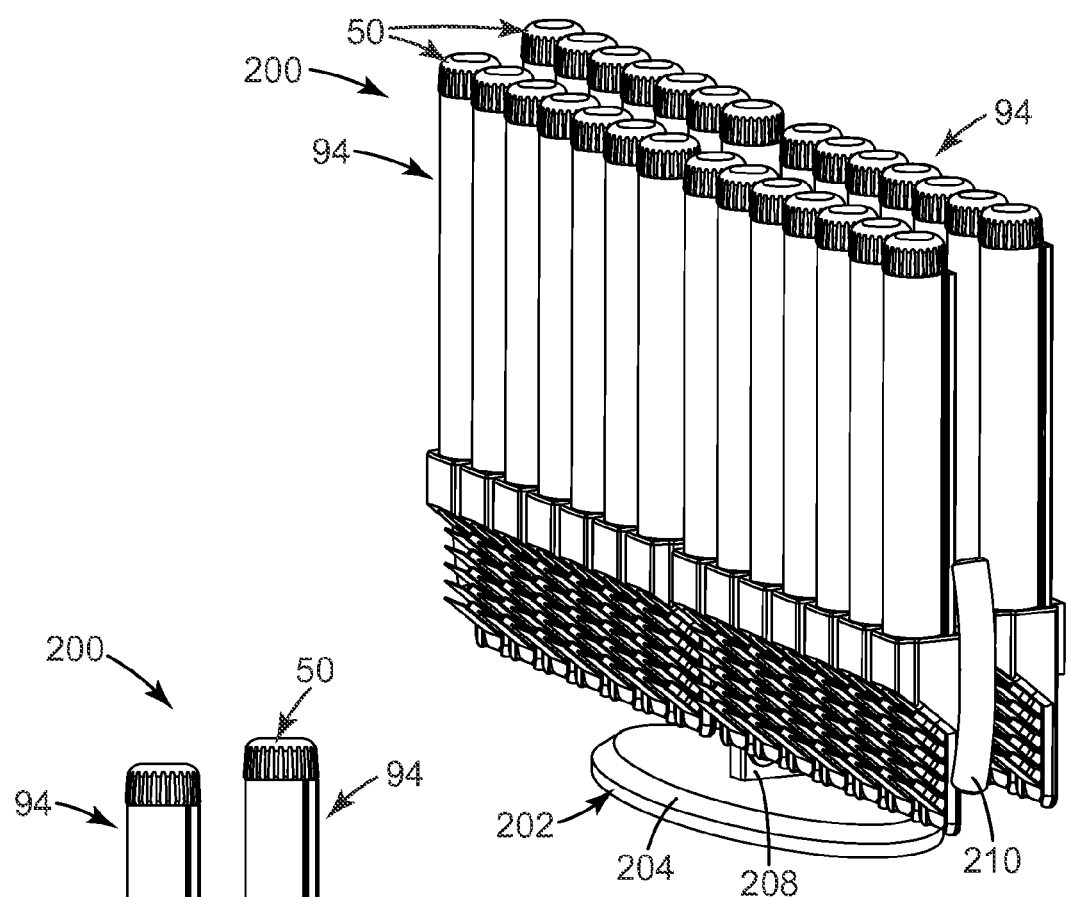
FIG. 12 is a perspective view of a dispensing system according to another embodiment of the invention, showing the system in a storage orientation.
Figure 13:
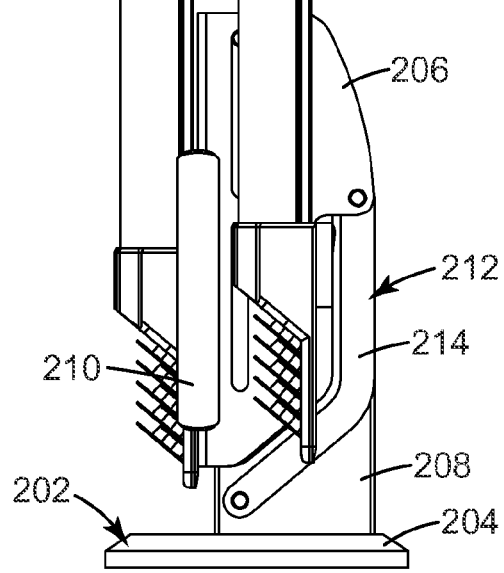
FIG. 13 is a side cross-sectional view of the dispensing system depicted in FIG. 12.
Figure 14:
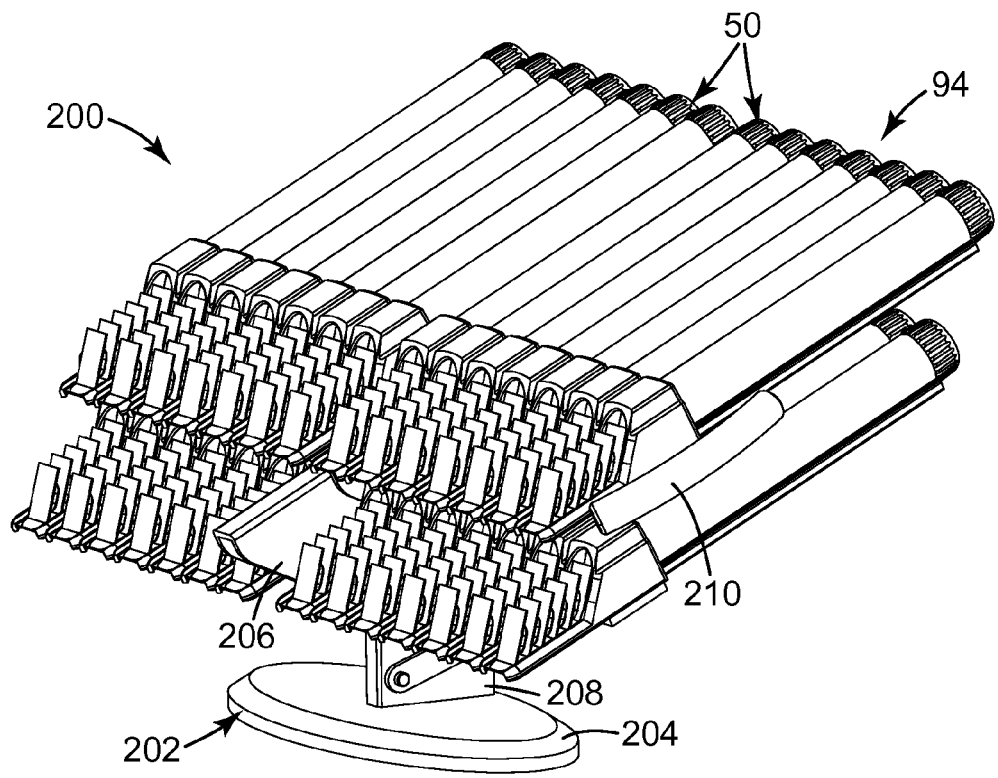
FIG. 14 is a perspective view of the dispensing system shown in FIGS. 12 and 13, except that the system is illustrated in an orientation for dispensing.
Figure 15:
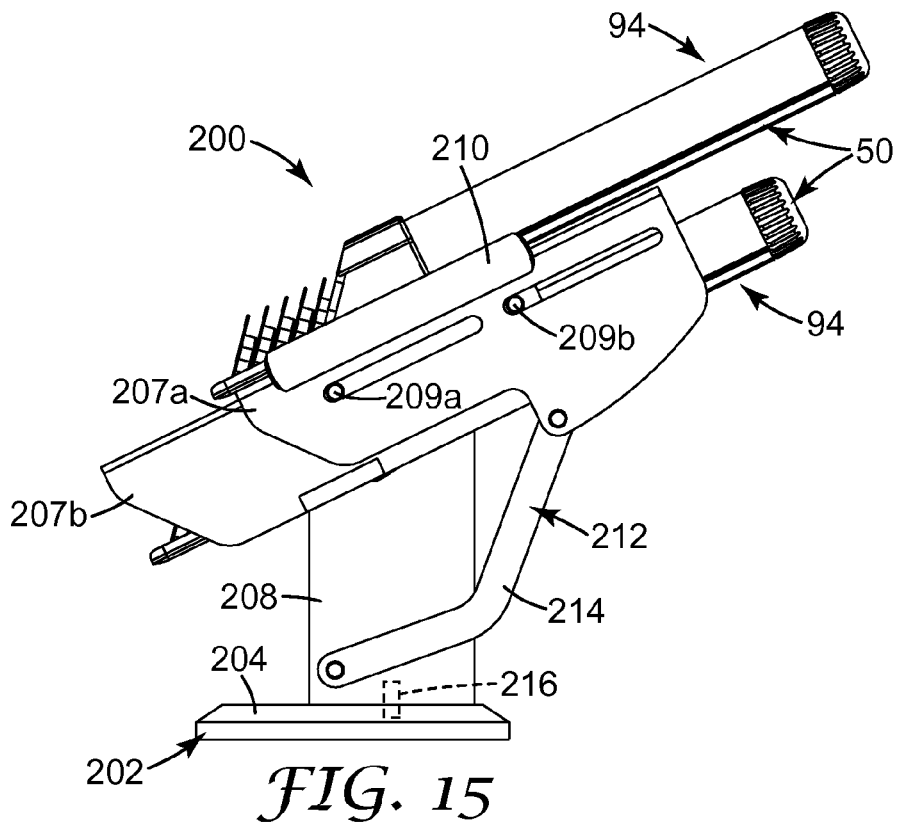
FIG. 15 is a side cross-sectional view of the dispensing system shown in FIG. 14.

A dispensing system 200 constructed in accordance with another embodiment of the invention is illustrated in FIGS. 12-15. The system 200 includes a base 202 with a stand 204 and an upstanding leg 208 connected to the stand 204. A carriage 206 is connected to the leg 208 and supports a number of dispenser arrays 94. The base 202 additionally includes a mechanism 212 for selectively moving the carriage 206 along with the arrays 94 between an upright storage orientation as shown in FIGS. 12-13 and an inclined orientation for dispensing as depicted in FIGS. 14-15.

In this embodiment, the carriage 206 includes two sections 207a, 207b that are slidably connected together for movement relative to each other in directions along the longitudinal axis of the supply tubes of the arrays 94. In FIG. 15, some of the dispensing assemblies 50 have been removed to better illustrate the sections 207a, 207b. The lower section 207b includes two pins 209a, 209b that are slidably received in slots of the upper section 207a. The mechanism 212 includes an angulated arm 214 that is connected at its lower end by a pivot to the leg 208 and is connected at its upper end to the upper section 207a of the carriage 206. The lower section 207b of the carriage 206 is pivotally connected to the leg 208 by the pin 209a. As the arrays 94 are moved from their upright storage positions as shown in FIGS. 12-13 and to their inclined dispensing orientations as shown in FIGS. 14-15, the arm 214 moves the upper section 207a of the carriage 206 in a rearward direction relative to the lower section 207b. As a result, the arrays 94 are arranged in a terraced orientation as shown in FIGS. 14-15 when the arrays 94 are inclined for dispensing.

Optionally, a pivotal connection 216 (shown in dashed lines in FIG. 15) comprising a pin is provided to couple the stand 204 to the leg 208. The pivotal connection 216 enables the carriage 206 along with the arrays 94 to be moved in an arc about a vertical axis for facilitating access to the arrays 94 from different directions as may be desired. Handles 210 extend along each side of the carriage 206 for facilitating rotational movement of the carriage 206 about a vertical axis and tilting movement of the carriage 206 between inclined and storage orientations.

As an alternative, the assemblies 50 shown in FIGS. 12-15 may be replaced with assemblies that are similar but include supply tubes with a rectangular configuration in cross-section. When the assemblies are in contact with adjacent assemblies, the rectangular configurations may facilitate disinfecting and cleaning the outer, exposed surfaces of the supply tubes. As an additional alternative, the assemblies 50 may be replaced with taller assemblies having an internal stack of two or more carrier strips 62 each connected to containers 64. As the lowermost carrier strip 62 in the stack is moved toward the dispensing head, the next adjacent carrier strip 62 in an upward direction descends to the bottom of the supply tube. Preferably, a slide is provided in the bottom of the supply tube for supporting and advancing the lowermost carrier strip toward the dispensing head.

A dispensing system 300 according to another embodiment of the invention is shown in FIGS. 16-20. The system 300 includes a number of dispensing arrays 94 as well as a base that comprises a pair of walls 303 that extend along opposite sides of the group of arrays 94. A carriage (not shown) is connected to the walls 303 and includes a spline for releasable connection to dispensing heads 78 of the arrays 94.

Figure 16:
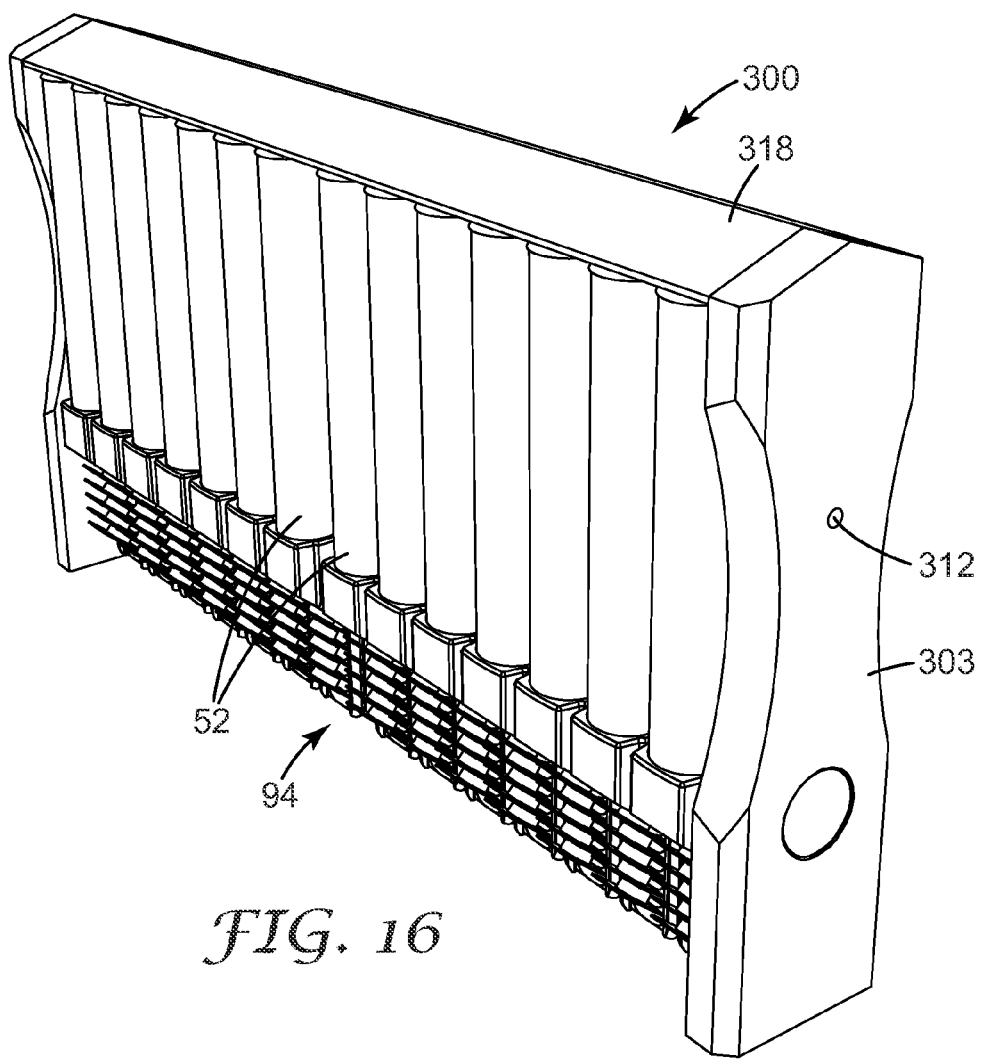
FIG. 16 is a perspective view of a dispensing system according to yet another embodiment of the invention.
Figures 17, 18:
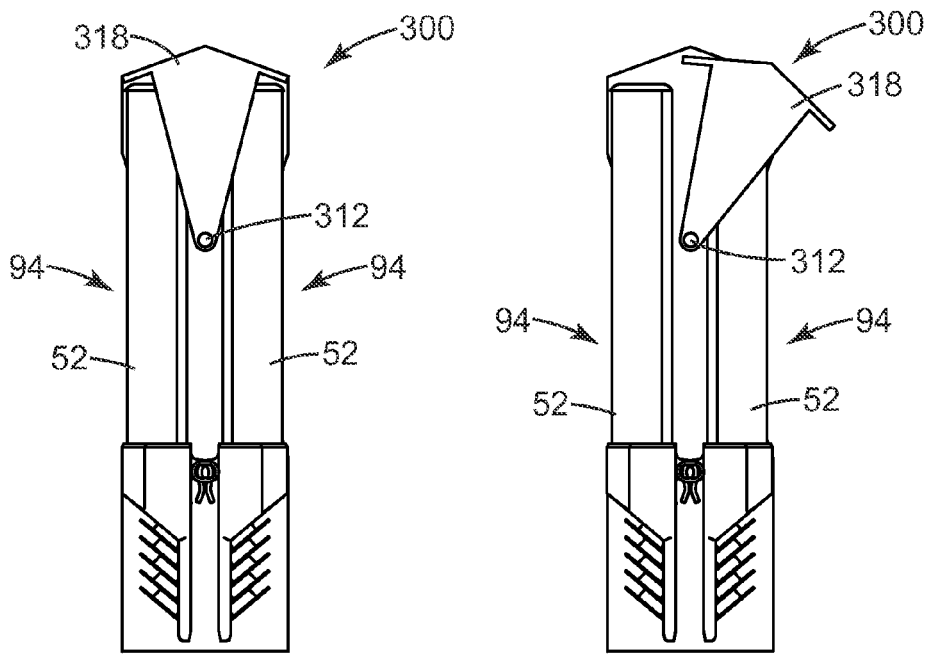
FIG. 17 is a side cross-sectional view of the dispensing system shown in FIG. 16.
FIG. 18 is a view somewhat similar to FIG. 17 except that a cover of the dispensing system has been moved to an orientation away from the outer ends of supply tubes of the system.
Figure 19:
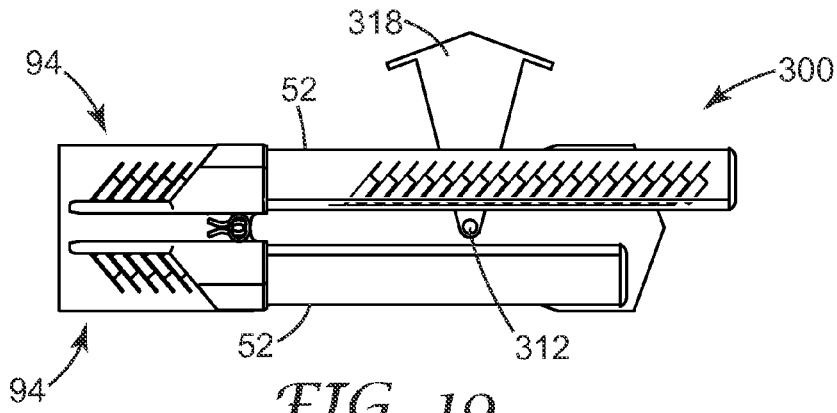
FIG. 19 is a view somewhat similar to FIGS. 17-18 except that the dispensing system is shown in an orientation as might be used for replacing one or more of the supply tubes.
Figure 20:
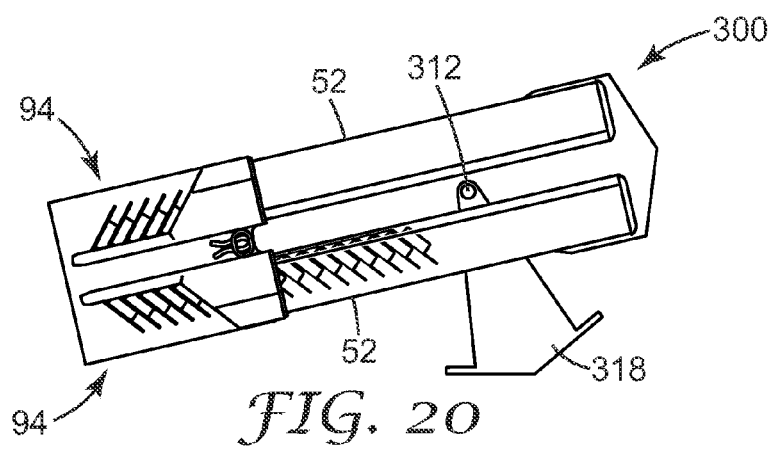
FIG. 20 is a view somewhat similar to FIGS. 17-19 except that the dispensing system is shown in an orientation as might be used during a dispensing operation.

The system 302 includes a cover 318 that has a generally hip-shaped roof and two arms that depend from the roof. The arms of the cover 318 are connected to the walls 303 by a mechanism 312 that comprises a pivotal connection. In FIGS. 16 and 17, the cover 318 is shown in a position completely covering the rear ends of the supply tubes 52. In FIG. 18, the cover 318 is illustrated in an exemplary position uncovering the rearward ends of some of the supply tubes 52 as may be desired to refill the uncovered tubes 52 with additional containers 64. In FIG. 19, the cover 318 has been moved to an out-of-the-way position so that the arrays 94 can rest in a horizontal orientation as may be preferred for refilling or replacement of the tubes 52. In FIG. 20, the cover 318 is shown in a depending position for supporting the arrays 94 in an inclined orientation for dispensing.

A dispensing system 400 according to yet another embodiment of the invention is depicted in FIGS. 21-25. The system 400 includes a number of dispensing arrays 94 as well as a base that comprises two sections 405, 407. Each of the sections 405, 407 includes two end walls 403 that extend along opposite sides of the arrays 94. Each section 405, 407 also includes a spline 496 that extends between the walls 403. The sections 405, 407 are releasably connected to each other by two leaf hinges 424 (see FIG. 23).

One of the arrays 94 of each section 405, 407 includes a spline 496 that is fixed on opposite ends to the walls 403 of the corresponding section 405, 407. The remaining array 94 of each section 405, 407 includes a spline (not shown) that is connected to a carriage 406 (see FIG. 25). The carriage 406 is pivotally connected to a handle 420, and in turn the handle 420 is pivotally connected to the walls 403 by a bar 422 (see FIGS. 21-22).

Figure 21:
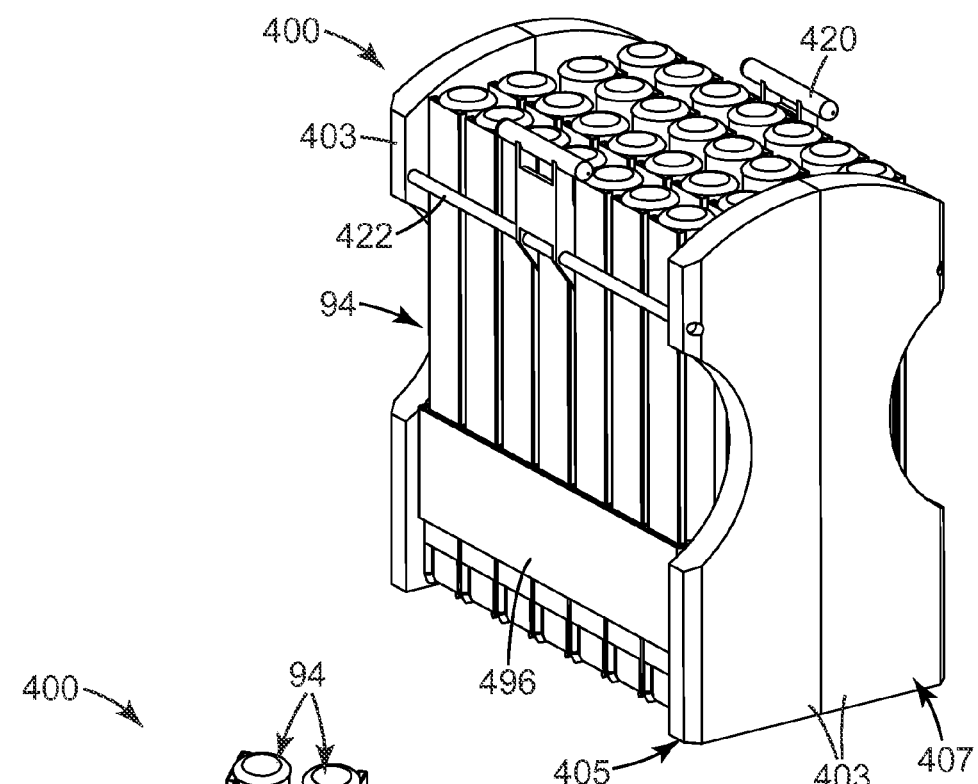
FIG. 21 is a perspective view of a dispensing system according to an additional embodiment of the invention, showing the system in an orientation as it might appear when stored.
Figure 22:
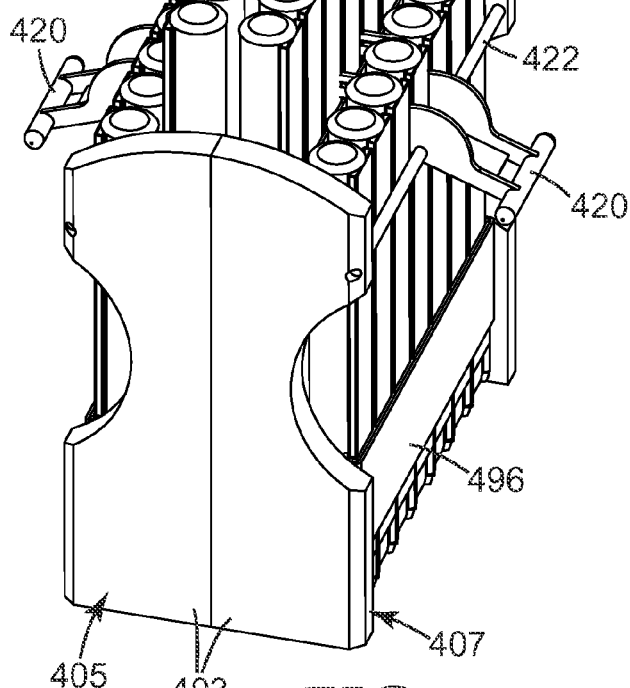
FIG. 22 is a perspective view of the dispensing system shown in FIG. 21 except that support legs of the dispensing system have been moved, causing dispenser arrays of the system to appear in a terraced orientation.

The sections 405, 407 of the system 400 are shown in their collapsed orientation in FIG. 21 as they might appear during storage. When it is desired to use the system 400 in a dispensing operation, the handles 420 are moved upwardly in an arc to the positions shown in FIG. 22. Movement of the handles 420 also moves the carriages 406 such that the inner array 94 of each section 405, 407 moves upwardly relative to the outer arrays 94.

Figure 23:
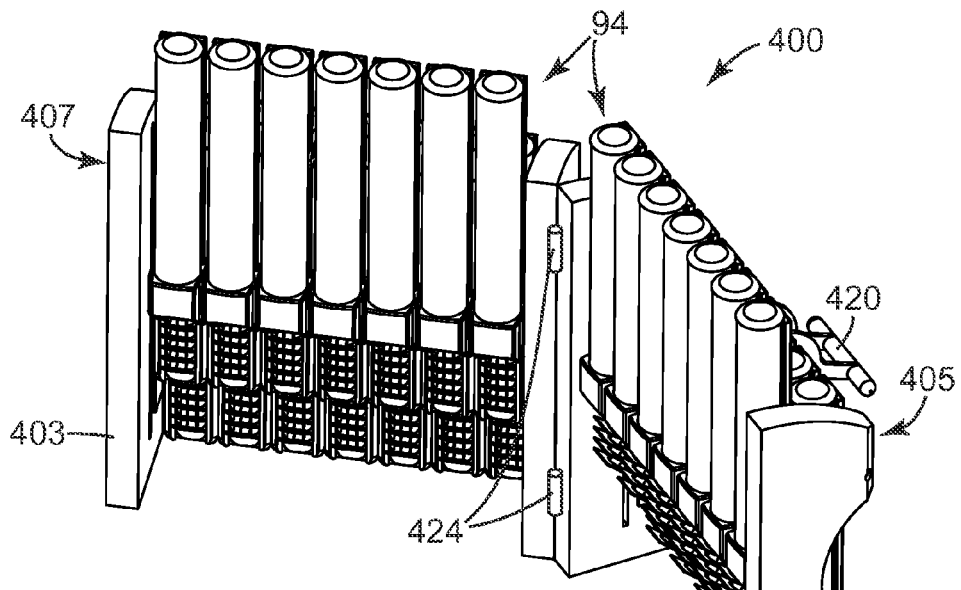
FIG. 23 is a perspective view of the dispensing system shown in FIG. 22 except that right and left sections of the system have been moved to an open orientation.
Figure 24:
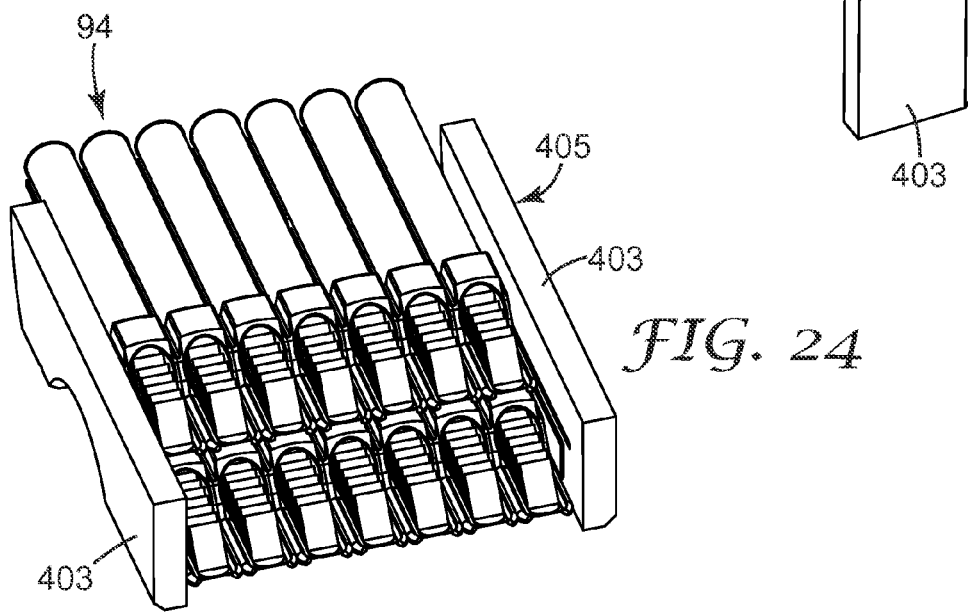
FIG. 24 is a perspective view of one of the sections depicted in FIG. 23, illustrating the section in an orientation as might be used for dispensing.
Figure 25:
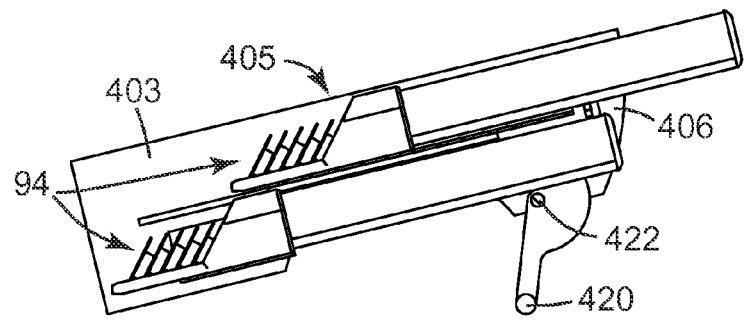
FIG. 25 is a side cross-sectional view of the dispensing section shown in FIG. 24.

FIG. 23 is an illustration of the sections 405, 407 when moved away from each other and to an open orientation about the axes of the hinges 424. Leaves of the hinges 424 can then be disconnected (for example, by removal of a pin) in order to detach the sections 405, 407 from each other. FIGS. 24 and 25 depict the section 405 alone as it might appear during a dispensing operation. In FIGS. 24 and 25, the section 405 is resting on the handle 420 which provides a mechanism for supporting the arrays 94 in an inclined orientation.

A dispensing system 500 constructed in accordance with another embodiment of the invention is illustrated in FIGS. 26-28. The system 500 includes a base 502 (not shown in FIG. 26) with a stand 504 adapted for mounting on a vertical surface, such as a cabinet or wall of a dental office. The system 500 also includes a mechanism 512 for moving an array 94 of the system 500 between a vertical orientation for storage as shown in FIGS. 26-27 and an inclined orientation for dispensing as shown in FIG. 28.

The mechanism 512 includes a first articulated arm 526 that is pivotally connected at one end to the stand 504 and is pivotally connected at the opposite end to a second articulated arm 528. An opposite end of the second arm 528 (i.e., remote from the pivotal connection with the first arm 526) is connected to a spline of the array 94. When the arms 526, 528 are folded together, the array 94 is in its upright orientation. Unfolding of the arms 526, 528 enables the array 94 to swing downward and toward the inclined orientation for dispensing.

Figure 29:
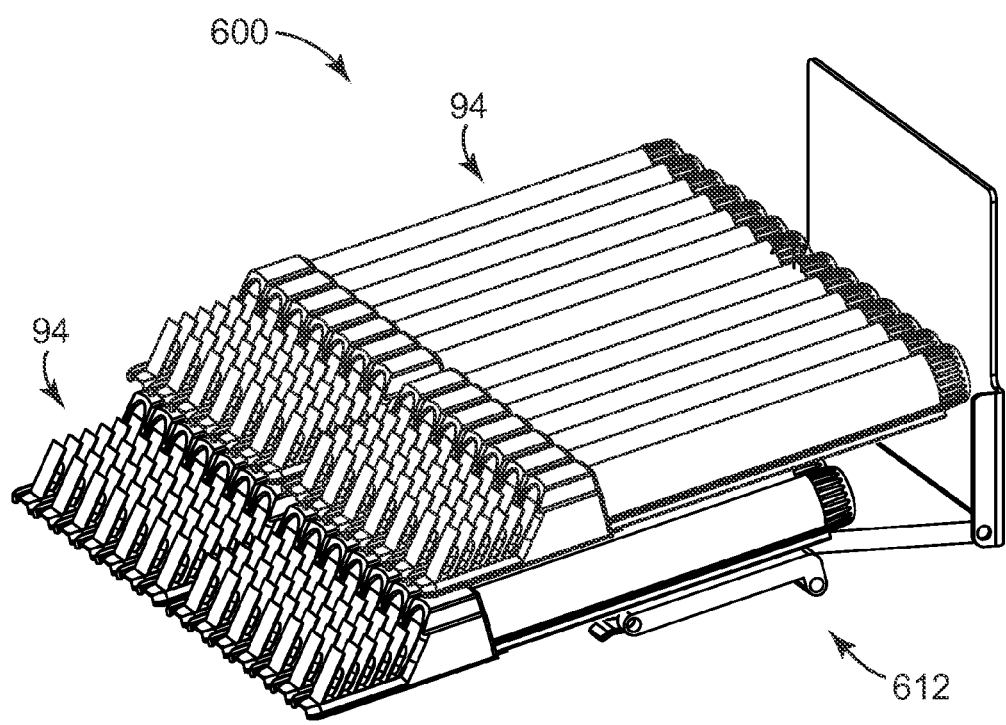
FIG. 29 is a perspective view of a dispensing system according to still another embodiment of the invention, showing the system in an orientation as it might appear during a dispensing operation.
Figure 30:
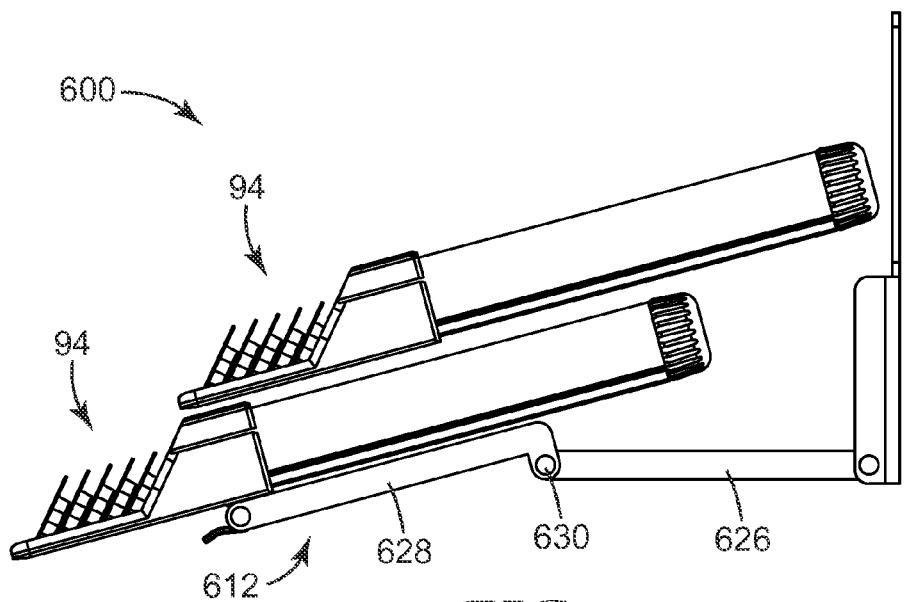
FIG. 30 is a side elevational view of the dispensing system depicted in FIG. 29.
Figure 31:
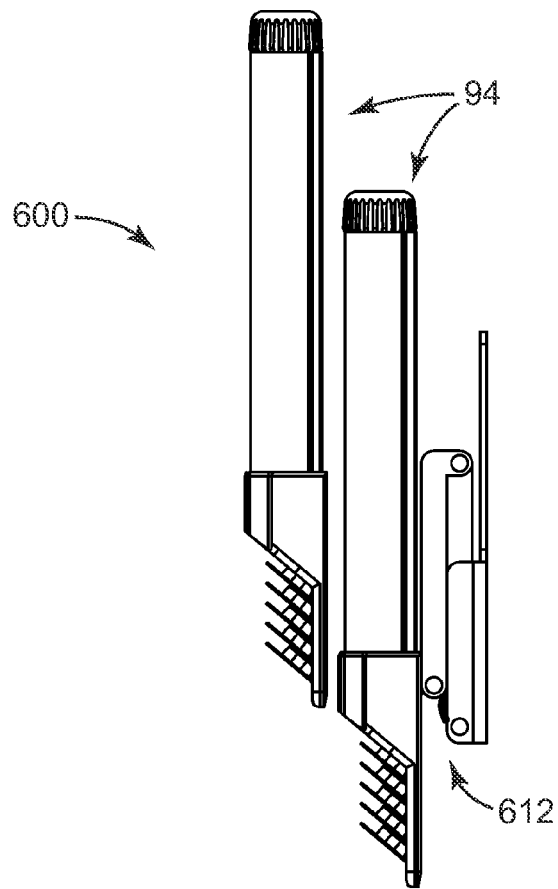
FIG. 31 is a view somewhat similar to FIG. 30 except that the dispensing system is shown in an orientation as it might appear when not in use.

A dispensing system 600 according to an additional embodiment of the invention is depicted in FIGS. 29-31. The system 600 is somewhat similar to the system 500 described above, but in this embodiment the system 600 includes two arrays 94 that are movable between an upright orientation for storage as shown in FIG. 31 and an inclined orientation for dispensing as shown in FIGS. 29-30. In addition, the arrays 94 are arranged in a terraced orientation when the arrays 94 are in the inclined orientation shown in FIGS. 29 and 30.

The position of the arrays 94 relative to each other is fixed in this embodiment of the invention. The system 600 includes a mechanism 612 that is similar to the mechanism 512 described above and includes two articulated arms 626, 628 that are connected together by a pivot 630. Since the arrays 94 of the system 600 are fixed relative to each other, the arrays 94 move together as a unit as the mechanism 612 moves the arrays 94 between the inclined orientation and the upright orientation. Optionally, the arms 626, 628 may be arranged such that the arm 626 extends in a horizontal direction while the arm 628 extends in an upright direction; in this arrangement, the arrays 94 are in upright orientation but spaced from the wall surface in order to facilitate re-loading of the supply tubes with additional containers.

As a further option, the pivot 630 may be constructed to releasably connect the arms 626, 628 together. The arm 628 may then be detached from the arm 626 and instead coupled to a base (not shown) that is adapted to sit atop a countertop or other horizontal surface. Such construction enables the practitioner to use the system 600 either as a wall-mounted assembly or as a tabletop-supported assembly as may be desired. Other types of releasably connections are also possible.

All of the patents and patent applications mentioned above are hereby expressly incorporated by reference into this disclosure. In addition, a number of alternative constructions for the presently preferred embodiments set out above as well as additional features may be apparent to those skilled in the art. Accordingly, the invention should not be deemed limited to the specific embodiments described in detail herein, but instead only by a fair scope of the claims that follow along with their equivalents.

The invention claimed is:

1. A dispensing assembly for dental articles comprising:
   a carrier strip having a generally flat configuration;
   a plurality of containers each releasably connected to the carrier strip;
   a plurality of dental articles each received in a respective one of the containers;
   a supply tube including a housing having a longitudinal axis and a chamber extending along the longitudinal axis, wherein the chamber includes a base portion having a generally rectangular configuration when viewed in reference planes perpendicular to the longitudinal axis and an upper portion having a generally circular configuration when viewed in reference planes perpendicular to the longitudinal axis, wherein the base portion is in communication with the upper portion and receives the carrier strip, wherein the carrier strip is slidable along the base portion in directions along the longitudinal axis, and wherein the containers extend into the upper portion; and
   including a dispensing head coupled to the supply tube, wherein the dispensing head includes at least one rail for guiding the movement of the carrier strip and also includes an opening for grasping one of the containers.

2. A dispensing assembly for dental articles according to claim 1 wherein the containers are oriented in a stacked arrangement and wherein each container extends at a non-zero angle relative to the carrier strip.

3. A dispensing assembly for dental articles according to claim 2 wherein each of the containers includes a cover having a tab, and wherein an adhesive releasably connects each tab to the carrier strip.

4. A dispensing assembly for dental articles according to claim 1 and including at least one additional carrier strip received in the supply tube and a number of containers releasably connected to each additional carrier strip.

5. A dispensing assembly for dental articles according to claim 1 and including at least one key connected to one of the supply tube and the dispensing head and at least one keyway connected to the other of the supply tube and the dispensing head.

6. A dispensing assembly for dental articles according to claim 5 wherein the supply tube includes a forward end, wherein the keyway comprises a slot in the forward end of the supply tube, and wherein the key comprises a cog that is connected to the dispensing head and is received in the slot when the supply tube is coupled to the dispensing head.

7. A dispensing system for dental articles comprising:
   an array of elongated supply tubes arranged along a row in side-by-side relationship to each other;
   a quantity of containers received in the supply tubes, each releasably connected to a carrier strip;
   a plurality of dental articles each received in a respective one of the containers; and
   a base for supporting the array of supply tubes, the base including a mechanism for selectively supporting the array in either an upright orientation for storage and alternatively in an inclined orientation for dispensing, wherein each supply tube of the array includes a housing having a longitudinal axis and a chamber extending along the longitudinal axis, wherein the chamber includes a base portion having a generally rectangular configuration when viewed in reference planes perpendicular to the longitudinal axis and an upper portion having a generally circular configuration when viewed in reference planes perpendicular to the longitudinal axis, wherein the base portion is in communication with the upper portion and receives the carrier strip, wherein the carrier strip is slidable along the base portion in directions along the longitudinal axis, and wherein the containers extend into the upper portion; and including a dispensing head coupled to the supply tube, wherein the dispensing head includes at least one rail for guiding the movement of the carrier strip and also includes an opening for grasping one of the containers.

8. A dispensing system for dental articles according to claim 7 wherein the mechanism includes at least one pivot for moving the array in an arc about a generally horizontal reference axis.

9. A dispensing system for dental articles according to claim 7 wherein the dispensing system also includes a number of caps each connected to a respective one of the supply tubes, and wherein each cap can be shifted relative to its respective supply tube in order to permit refilling of the supply tube with additional containers.

10. A dispensing system for dental articles according to claim 8 wherein the supply tubes each include an upper end when the array is in its upright orientation, wherein the base includes a cover, wherein the mechanism includes at least one pivot connected to the cover for moving the cover relative to the array between a first position extending over the ends of the supply tubes and a second position remote from the ends of the supply tube, and wherein the cover when in its second position supports the array in the inclined orientation for dispensing.

11. A dispensing system for dental articles according to claim 10 wherein the cover when in its second position enables access to the upper end of the supply tubes to permit refilling of the supply tubes with additional containers.

12. A dispensing system for dental articles according to claim 7 wherein the dispensing system additionally includes an elongated spline connected to the base and a plurality of connectors for releasably connecting the dispensing heads to the spline.

13. A dispensing system for dental articles according to claim 12 wherein the connectors comprise clips having an inverted, generally "U"-shaped configuration when the array is in an upright orientation.

14. A dispensing system for dental articles according to claim 7 wherein the dispensing system includes a second array of supply tubes, wherein the mechanism is operable to move both arrays between upright orientations and inclined orientations, and wherein the arrays when in an inclined orientation are also in a terraced orientation relative to each other.

15. A dispensing system for dental articles according to claim 7 wherein the base includes at least one leg connected to the array and a stand that is pivotally connected to the at least one leg for moving the array in an arc about a generally vertical axis.

16. A dispensing system for dental articles according to claim 7 wherein each supply tube is color-coded to indicate one or more characteristics of the dental articles in the containers.

* * * * *